(12) United States Patent
Zellerhoff

(10) Patent No.: US 7,515,677 B2
(45) Date of Patent: Apr. 7, 2009

(54) METHOD FOR X-RAY IMAGE RECORDING OF A NON-CENTRIC IMAGING AREA USING AN X-RAY IMAGING SYSTEM, AND X-RAY IMAGING SYSTEM

(75) Inventor: Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/901,616

(22) Filed: Sep. 18, 2007

(65) Prior Publication Data

US 2008/0123805 A1 May 29, 2008

(30) Foreign Application Priority Data

Sep. 29, 2006 (DE) .......................... 10 2006 046 692

(51) Int. Cl.
*A61B 6/00* (2006.01)
(52) U.S. Cl. ............................ 378/4; 378/196; 378/197
(58) Field of Classification Search ...................... 378/4, 378/8, 11, 15, 19, 62, 95, 195–197, 198, 378/205
See application file for complete search history.

(56) References Cited

U.S. PATENT DOCUMENTS

| 4,324,978 | A | * | 4/1982 | Kalender et al. ................ 378/4 |
| 2006/0120507 | A1 | * | 6/2006 | Brunner et al. ................ 378/62 |
| 2008/0240363 | A1 | * | 10/2008 | Grebner et al. .............. 378/198 |

* cited by examiner

*Primary Examiner*—Edward J Glick
*Assistant Examiner*—Mona M Sanei

(57) ABSTRACT

There is described a method using an X-ray imaging unit, which has an arched support for the X-ray source and the X-ray detector. In the method, in a scan carried out by moving the support around an examination object a plurality of X-ray images of an area of interest are recorded using different projection angles, from which a three-dimensional image of the area of interest can be reconstructed. In this case the X-ray focus of the X-ray source is guided on a segment of a circular path of at least 180° around the examination object. In the case of a non-centric location of the area of interest, the support is rotated in such a manner prior to each of the X-ray imaging processes around an axis of rotation passing through the X-ray focus that the central ray of the X-ray beam for the X-ray imaging processes passes through the center of the area of interest.

16 Claims, 3 Drawing Sheets

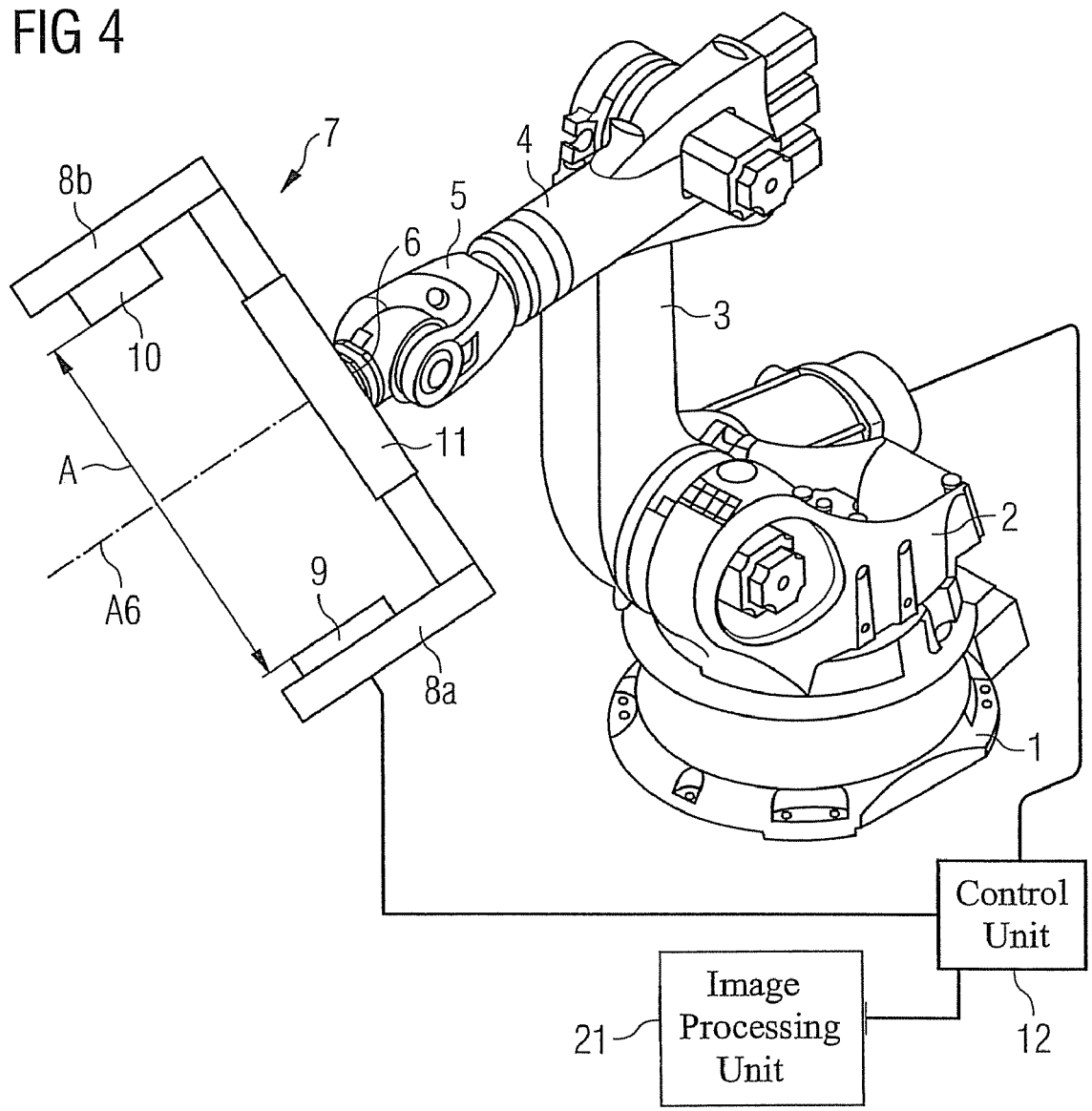

METHOD FOR X-RAY IMAGE RECORDING OF A NON-CENTRIC IMAGING AREA USING AN X-RAY IMAGING SYSTEM, AND X-RAY IMAGING SYSTEM

CROSS REFERENCE TO RELATED APPLICATIONS

This application claims priority of German Patent Office application No. 10 2006 046 692.6 DE filed Sep. 29, 2006, which is incorporated by reference herein in its entirety.

FIELD OF INVENTION

The present invention relates to a method for X-ray image recording using an X-ray imaging unit which has an X-ray source and an X-ray detector situated opposite the X-ray source on an arched support, with the result that an X-ray beam emitted from an X-ray focus at the X-ray source strikes the X-ray detector. The method in question is one in which during a scan carried out by moving the support around an examination object positioned between the X-ray source and the X-ray detector a plurality of X-ray images of an area of interest of the examination object are recorded using different projection angles, from which a three-dimensional image of the area of interest can be reconstructed. The invention also relates to an X-ray imaging system which is designed for carrying out the proposed method.

BACKGROUND OF INVENTION

C-arm units are widely used in medical applications. With regard to these systems, the X-ray detector and the X-ray source are mounted opposite one another on a so-called C-arm which is designed to perform a rotational movement. This means that the imaging system with the X-ray source and the X-ray detector can rotate around a rotation center, the so-called isocenter of the C-arm system. In this manner, not only two-dimensional X-ray images can be obtained when using modem C-arm systems but, by rotating the imaging system around the patient, three-dimensional, CT-like images or cross-sections can also be obtained. The image reconstruction of the three-dimensional images or of the cross-sections from the X-ray images recorded using different rotation angles or projections takes place in a similar manner to a computer tomograph (CT). One rotation of the C-arm around the patient through an angle range of 180° plus the fan angle of the X-ray beam is adequate for this purpose. Soft body parts or, through subtraction of contrast agent images and native images, angiograms can thus be represented three-dimensionally. A C-arm unit of such a type is described in US 2006/0120507 A1 for example.

In addition to these common C-arm systems, robot-guided C-arm systems are also known for example from DE 10 2005 012 700 A1, in which a C-arm with an X-ray source and an X-ray detector situated opposite the X-ray source is coupled to the hand of a robot which moves this X-ray recording system around the object of interest in order to record the two-dimensional X-ray images.

The X-rayed target area, of which a three-dimensional image is subsequently obtained by means of reconstruction, is restricted as a result of the size of the beam cone of the X-ray beam. The size of the beam cone is in turn coordinated with the size and the distance of the X-ray detector, as a rule a flat detector. The target area of interest must lie in the isocenter of the C-arm system in order that it can be imaged by the imaging system for each rotation or projection angle. With regard to target areas of interest in medical imaging, which are located centrally in the patient cross-section, this condition is met without further ado. However, if other areas are to be represented, then problems result on account of the above condition. It is thus not possible in many practical situations, for example with regard to vertebroplasty or kyphoplasty, to carry out the rotation of the C-arm on a circular path around the desired imaging area since collisions would occur in this case between the C-arm and the patient, the patient support or instruments in use.

SUMMARY OF INVENTION

An object of the present invention consists in setting down a method and an X-ray imaging system for carrying out the method, which also allow three-dimensional imaging of areas of an object which cannot be brought centrically into the circular path described by the focus of the X-ray source in the case of conventional C-arm systems.

This object is achieved by the method and the X-ray imaging system as claimed in independent claims. Advantageous embodiments of the method and of the X-ray imaging system are set down in the subclaims or can be taken from the following description and also from the exemplary embodiments.

With regard to the proposed method for X-ray image recording, an X-ray imaging unit is used which an has an X-ray source and an X-ray detector situated opposite the X-ray source on an arched support, with the result that an X-ray beam emitted from an X-ray focus at the X-ray source strikes the X-ray detector, if applicable after passing through an examination object positioned between them. In this situation, arched can be understood to include both round and also angular arrangements, for example C-shaped, U-shaped, V-shaped or similar supports, in which the X-ray tube and the X-ray detector are secured to two opposite elements. With regard to the present method, as a result of a movement of the support around an examination object positioned between the X-ray source and the X-ray detector a plurality of X-ray images of an area of interest of the examination object, from which a three-dimensional image of the area of interest can be reconstructed, are recorded in a scan from different projection angles. During this movement, the X-ray focus is guided on a segment of a circular path of at least 180° around the examination object, whereby the X-ray images are recorded at different positions of the X-ray focus on the circular path segment. The method is characterized by the fact that in the case of a non-centric location of the area of interest, in which case the central point of the circular path of the X-ray focus is situated non-centrically in the area of interest, the support is rotated in such a manner prior to each of the X-ray imaging processes around an axis of rotation passing through the X-ray focus that a central ray of the X-ray beam for the X-ray imaging processes passes through the center of the area of interest. In this situation, the axis of rotation passing through the X-ray focus for this additional rotational movement of the support is perpendicular to the plane of the circular path of the X-ray focus. The center of the area of interest is understood to be the geometric center in the plane of the circular path.

With regard to the proposed method, in addition to the movement of the X-ray focus on the circular path around the area of interest the support is thus pivoted around the X-ray focus or the X-ray source in such a way that the central ray of the X-ray beam passes through the center of the area of interest during each X-ray imaging process. In this manner, the area of interest always lies within the X-ray beam for each of the X-ray images even in the case of a non-centric location, with the result that no images are truncated. In this situation, the additional pivoting around the axis of rotation by the X-ray focus can for example be carried out immediately before each X-ray imaging process. By preference however, this adjustment movement occurs continuously and in synchronism with the rotational movement of the X-ray focus around the examination object. Since with regard to the different X-ray images the X-ray focus, as also in the case of the known X-ray image systems from the prior art, still moves on a circular path or a segment of a circular path around the examination object, the same algorithms can be used for the 3D image reconstruction, for example an algorithm for simple filtered back-projection, such as is also the case with regard to the systems from the prior art having a centrically situated area of interest. Suitable reconstruction algorithms are known to the person skilled in the art and can for example also be taken from the literature references quoted in DE 10 2004 057 308 A1.

The adjustment movement required in addition to the movement of the X-ray focus or of the X-ray tube on a circular path around the examination object can be carried out by using a suitable manipulator arm, on which the support bearing the X-ray source and the X-ray detector is secured, which can be moved in a versatile manner. By preference, a robot arm is used for this purpose, an industrial robot for example.

With the present method, even in the case of smaller areas of interest which are not situated centrically within the circular path of the X-ray focus a dose reduction is achieved for the patient when the X-ray beam is collimated accordingly to the smaller area. Through this collimation, the angle of beam spread of the X-ray source is restricted with the aid of diaphragms and the imaging area is thereby made smaller and the patient dose reduced.

If a plurality of scans having identical focus positions but different imaging areas are taken, then prior to the reconstruction these can be projected into a common, so-called virtual projection. To this end, the recorded image data for the X-ray images, which have been recorded at the same position of the X-ray focus on the segment of the circular path, are merged in such a way as if they originated from a single image taken with a sufficiently large detector. If individual areas of the virtual projection are contained in a plurality of real projections, then a noise reduction can be achieved in the image by averaging the multiple image data present for these areas. The subsequent image reconstruction of the three-dimensional image is carried out on the basis of the merged image data.

This procedure can also be utilized in order to enlarge the overall imaging area. To this end, a plurality of overlapping imaging areas are chosen and recorded in successive scans, whereby the projections of the individual scans are then merged again in a virtual projection prior to the reconstruction. Here too, with regard to this virtual projection, the image data from X-ray images from the different scans, which have been recorded with the X-ray focus at the same position, are merged. In this manner, during the later image reconstruction using the merged image data, artifacts resulting from truncated projection images can be avoided.

In a further advantageous embodiment of the present invention, a plurality of scans are likewise performed. In this situation, one of these scans takes place at a greater angle of beam spread of the X-ray beam cone, for example without collimation or with only a slight collimation, with the result that the cross-section of the examination object still lies completely within the X-ray beam cone. During one or more further scans the X-ray beam is then more highly collimated according to the particular area of interest. The scan with low or no collimation is carried out with a lower X-ray dose than the scans of the areas of interest with a collimated X-ray beam. If the image data from the different scans is then merged in the manner specified above, then a three-dimensional image of the examination area can be obtained, in which the areas of interest are embedded with a high image quality in surrounding areas of lower image quality and no artifacts whatsoever occur as a result of truncated object areas. In this situation, the merging of the image data occurs in the overlapping areas by means of weighted averaging, in which the image data from the scans with a higher collimation and a higher X-ray dose have a greater weighting than the image data from the scan with a lower X-ray dose.

The proposed X-ray imaging system comprises an arched support, on which are mounted an X-ray source and an X-ray detector situated opposite the X-ray source such that an X-ray beam emitted from an X-ray focus at the X-ray source strikes the X-ray detector. The support is secured to a manipulator arm, by means of which the support can be moved around an examination object positioned between the X-ray source and the X-ray detector. The X-ray imaging system has a control unit for the purpose of X-ray image recording, which in addition to controlling the X-ray tube and the X-ray detector for the X-ray image recording controls the manipulator arm during the X-ray image recording according to the proposed method. Through this control facility the manipulator arm moves the support such that the X-ray focus is guided on a segment of a circular path of at least 180° around the examination object during a scan in order to record a plurality of X-ray images of an area of interest of the examination object from different projection angles, from which a three-dimensional image of the area of interest can be reconstructed. Furthermore, the support is moved by the manipulator arm during a scan in such a manner that, in the case of a non-centric location of the area of interest, whereby the central point of the circular path is situated non-centrically in the area of interest, it is rotated prior to each of the X-ray imaging processes around an axis of rotation passing through the X-ray focus such that a central ray of the X-ray beam passes through the center of the area of interest during the X-ray imaging processes. In this situation, the control unit preferably controls the manipulator arm such that the rotation occurs in synchronism with the guidance of the X-ray focus on the circular path. The angle of rotation required in each case for the different focus positions on the circular path is in this case preferably determined prior to carrying out the respective scan. This can be done by way of one or more overview X-rays of the object which are displayed for the user on the visual display unit. The user can then mark the area of interest in these displayed images. Since the dimensions of the support with the X-ray tube and the X-ray detector and also the position of the examination object with respect to one another are known, the rotational movement required in each case can then be calculated using purely geometric means by a calculator unit and passed to the control unit.

By preference, the proposed X-ray imaging system in question is a robot-guided C-arm system in which the manipulator arm is the arm of a robot. The robot can for example have six axes of rotation. In one embodiment this can be an articulated robot, as is used in production lines in the automobile industry.

The proposed X-ray imaging system preferably includes an image processing computer which carries out the merging described in accordance with one or more embodiments of the method of the image data from a plurality of scans in accordance with this method and performs the 3D reconstruction on the basis of the merged image data. In this situation, this merging and image reconstruction can be performed by a suitable software module.

BRIEF DESCRIPTION OF THE DRAWINGS

The present method and the associated X-ray imaging system will be described again in brief in the following with reference to an exemplary embodiment in conjunction with the drawings. In the drawings:

FIG. 4 shows a perspective view of a recording device according to the invention.

DETAILED DESCRIPTION OF INVENTION

Figure 1:
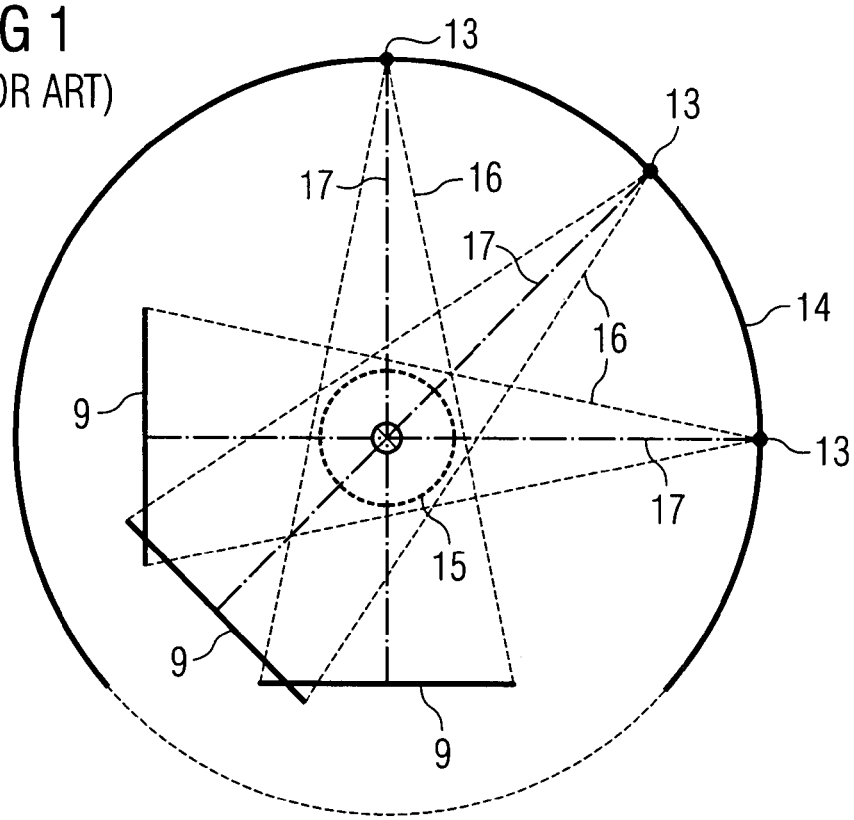
FIG. 1 shows a schematic representation of a recording situation in which the area of interest is situated centrically within the focus path.

With regard to known C-arm systems, the rotation of the C-arm with the X-ray tube and the X-ray detector takes place around a fixed rotation center, in which the area of interest of the examination object must also be situated. In this situation, the examination object is usually a patient who is suitably positioned on a patient support. FIG. 1 schematically illustrates such a recording situation in which the X-ray focus 13 of the C-arm system is guided on a segment of a circular path, also referred to in the following as the focus path 14. As a result of the rotation of the support with the X-ray tube around the fixed rotation center the X-ray detector 9 also moves on a corresponding circular path, as indicated in FIG. 1. For error-free image reconstruction the area of interest 15 must, for each projection or X-ray imaging process, lie within the beam cone 16 of the X-ray beam which is emitted by the X-ray focus 13 in the direction of the X-ray detector 9. In this situation, the central ray 17 of the X-ray beam passes through the rotation center in each case, which also represents the center of the area which can be imaged without errors, in the present case the area of interest 15. The size of this imaging area is limited by the size of the detector and the beam cone of the X-ray beam. In this situation, FIG. 1 indicates different positions of the X-ray focus 13 on the focus path 14 at which an X-ray image recording takes place. From the X-ray image data recorded in this manner, three-dimensional images of the area of interest 15 can then be reconstructed using the known methods of filtered back-projection.

Problems result however when the area of interest 15 lies non-centrically within the focus path 14. In this case, this area is not completely covered at every projection angle by the X-ray beam, with the result that truncated projections occur. These truncated projections lead to disruptive image artifacts in the subsequent three-dimensional image of the area of interest. With regard to the present method, these truncated projections are prevented by an additional rotational movement of the support around an axis through the current focus position, as is indicated schematically in FIG. 2. With regard to this procedural method, the X-ray focus 13 is still guided on the segment of a circular path, the focus path 14. However, this is carried out by using a manipulator arm, on which the C-arm or support is mounted, which is extremely versatile in its movement capabilities.

Figure 2:
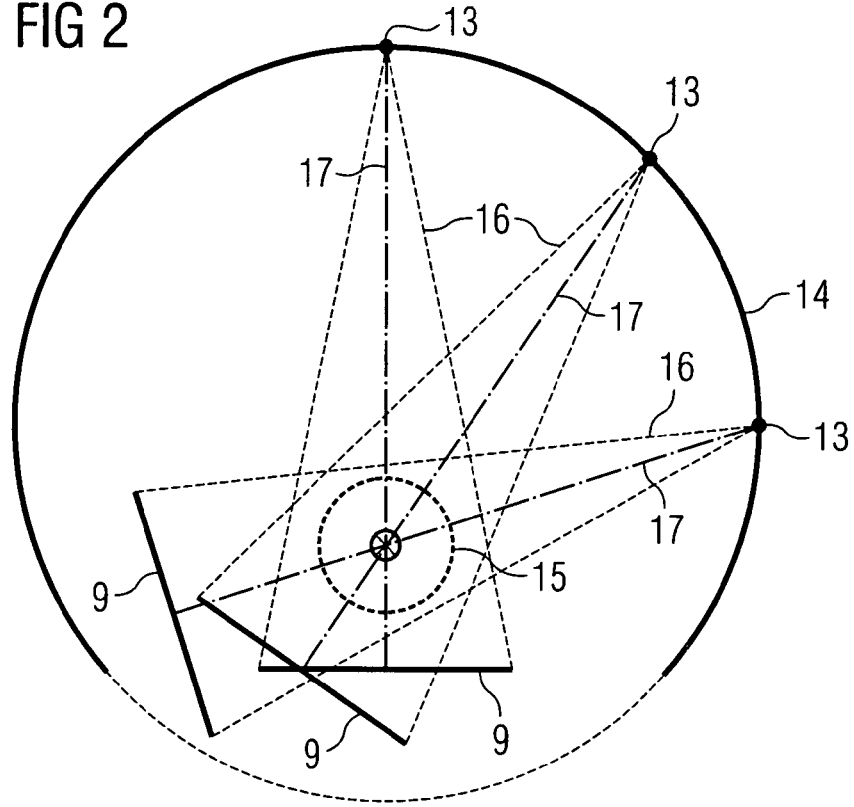
FIG. 2 shows a schematic representation of the recording situation with regard to the present method, in which the area of interest is situated outside the center of the focus path.

When a scan is performed for X-ray image recording, the positions of the X-ray source or of the X-ray focus 13 for the individual imaging processes—as in the case of the conventional scan—are equally spaced on the circular path. The perpendicular from the X-ray source to the detector center, which represents the central ray 17, no longer passes through the central point of the focus circle however. The support is in fact pivoted around the X-ray source or the X-ray focus during the scan in such a manner that the perpendicular passes through the central point of the desired imaging area 15. With this arrangement the detector no longer moves on a circular path but still lies within the focus path 14. The positions of the detectors generally lie outside a circle which the detector would describe when X-raying centrically located target areas. It is therefore possible to image areas which lie very close to this previous detector circle. FIG. 2 shows the three recording situations with regard to the three focus positions, which have already been illustrated in Figure. As can be seen from FIG. 2, it is however possible with the present method by means of appropriate rotation of the support around an axis through the X-ray focus 13 (and perpendicular to the viewing plane) to bring the area of interest 15 into the beam cone 16 for each of the focus positions with the result that the area of interest 15 is completely covered at all times for every X-ray imaging process even in the case of the non-centric location shown. Since the X-ray focus 13 continues to be guided on a circular path, the recording geometry illustrated here permits the 3D reconstruction of an image from the obtained projection data with the aid of an algorithm for simple filtered back-projection, such as is also normal for a centrically situated imaging area.

Figure 3:
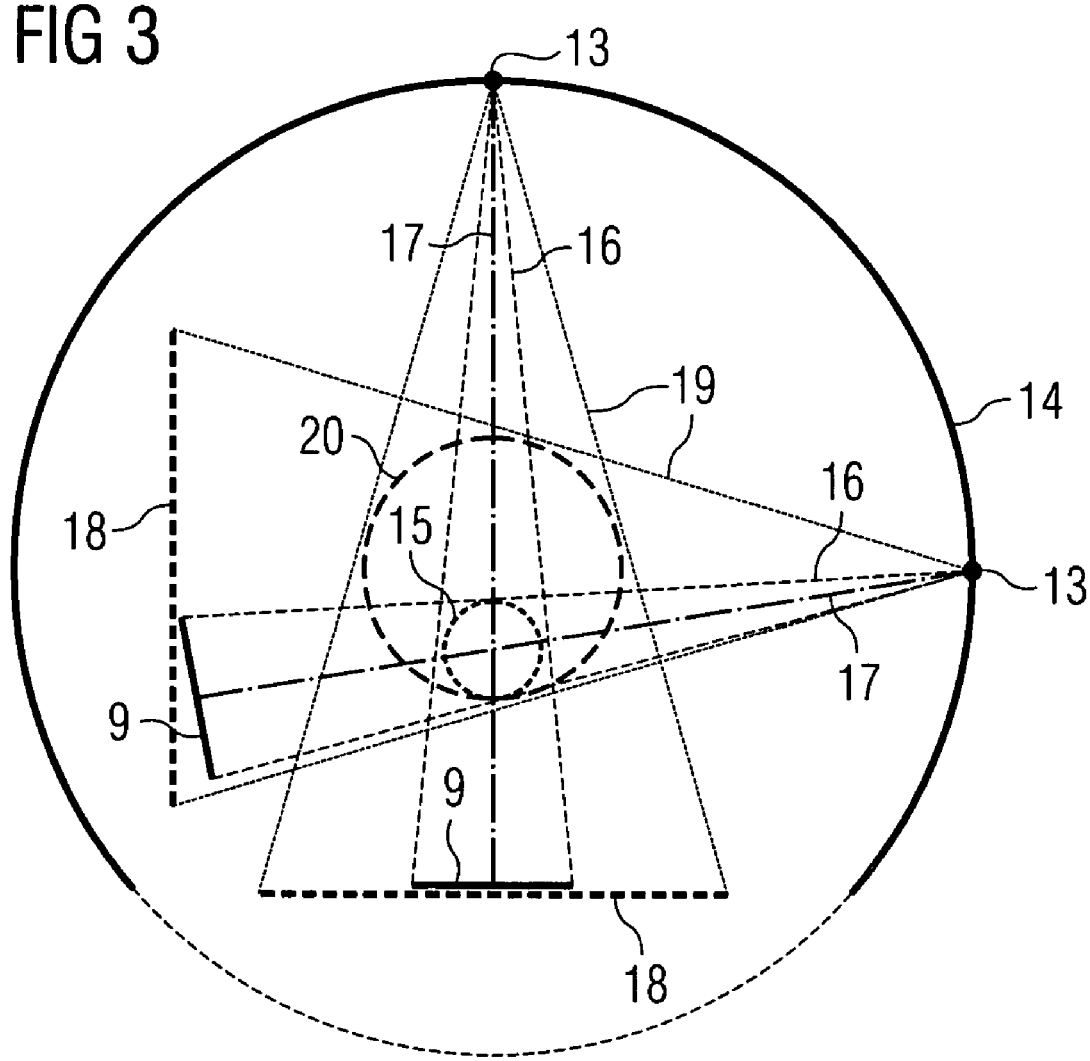
FIG. 3 shows a schematic representation of a further embodiment of the present method, in which the image data from a plurality of scans is merged.

If a plurality of scans having identical focus positions but different imaging areas are taken, then prior to the reconstruction these can be projected into a common virtual projection. This is illustrated by way of FIG. 3. This figure shows two focus positions with regard to the X-ray image recording of an area of interest 15 for one scan. If further scans are carried out for areas situated beside the area 15, then the image data from the scans can be merged as if a single scan had been carried out with a larger detector, referred to as a virtual detector 18. If individual areas of the virtual projection are contained in a plurality of real projections, then a noise reduction can be achieved in the image by averaging the respective image data in this area.

This makes it possible for example to record the maximum imaging area (without collimation) at a low dose in order to avoid artifacts resulting from truncated projection images, and to subsequently record one or more smaller imaging areas (with collimation of the X-ray cone) with a high dose in order to achieve maximum image quality (low noise) in these areas. In this situation, the entire examination area must naturally lie within the beam cone with regard to each projection at a low dose. Through a weighted averaging of the data on the virtual detector 18 a reconstruction of the entire imaging area at low quality is obtained, into which sub-areas of very high image quality are embedded. Artifacts caused by truncated projections with regard to the collimated projections can be avoided in this way. Thus, the beam cone 19 drawn in FIG. 3 can for example be the beam cone of the X-ray beam without collimation, while the narrower beam cone 16 is obtained by collimation from the X-ray source. In this situation, the area of interest 15 is embedded into an image of the examination object 20, whereby the area of interest 15 is depicted with a distinctly better image quality than the remaining area of the examination object 20.

The proposed method permits highly flexible 3D imaging of anatomical structures with the aid of flexible C-arm X-ray units. The capability to freely define an imaging area within the circular focus path permits the use of 3D imaging even when patient positioning is awkward and additional equipment is in use whilst avoiding collisions between the C-arm and instruments, patient or patient support. The combination of a plurality of scans makes it possible to extend the maximum imaging area and/or to reduce the overall patient dose by defining different imaging areas with a different recording dose (efficient dose utilization).

The recording geometry for carrying out the proposed method can for example be implemented by mounting a C-arm on a robot arm. Such an embodiment is illustrated schematically in the example shown in FIG. 4. This figure shows a perspective view of an example of a suitable X-ray imaging system according to the present invention. The system comprises a known robot having six rotational axes. A carousel 2 capable of rotating around a first axis of rotation is fitted on a base frame 1 which for example can be permanently mounted on the floor of an operating room. A rocker 3 capable of pivoting around a second axis of rotation is mounted on the carousel 2. An arm 4 capable of rotating around a third axis of rotation is secured to the rocker 3. A robot hand 5 capable of rotating around a fourth axis of rotation is fitted at the end of the arm 4. The hand 5 has an interface 6 for connecting a tool which by way of the interface 6 is capable of rotating around an axis of rotation and capable of pivoting around a fifth axis of rotation running perpendicular to it. A support generally designated by the reference character 7 is connected to the interface 6 of the hand 5.

In the present example, the support 7 is designed in the nature of a U-profile with two side elements 8a, 8b situated opposite one another. On the first side element 8a is mounted an X-ray detector 9 and on the second side element 8b an X-ray source 10 in an opposing arrangement. The first side element 8a and the second side element 8b can be mounted to be capable of linear motion with respect to a central element 11 of the support, with the result that the distance A between the X-ray detector 9 and the X-ray source 10 can be adjusted.

The control of the robot for moving the image recording system formed by an X-ray source 10 and an X-ray detector 9 according to the present method is effected by way of the control unit 12 which also handles the image recording with the image recording system. The control unit 12 controls the robot according to the method described above for image recording and adjustment of the support.

The reconstruction of the obtained projection images to produce a three-dimensional data record can be implemented in the form of software on a universal computer, for example the image processing computer 21 indicated in FIG. 4, or in the form of special hardware. It is possible to use both an algorithm for filtered back-projection and also an iterative algorithm (for example the ART method described on pages 283 and 284 of the book "Principles of Computerized Tomographic Imaging" by Kak & Slaney). The combination of projection images from different scans is suitably carried out by projecting the real projection data into a combined virtual projection prior to the reconstruction.

The invention claimed is:

1. A method for X-ray image recording using an X-ray imaging unit, comprising:
providing the X-ray unit, wherein the X-ray unit has an X-ray source and an X-ray detector opposite the X-ray source on an arched support, wherein an X-ray beam emitted from an X-ray focus of the X-ray source strikes the X-ray detector;
recording a plurality of X-ray images during a scan of an area of interest of an examination object using different projection angles, wherein during the scan the support is moved around the examination object, wherein the examination object is positioned between the X-ray source and the X-ray detector, and wherein during the scan the X-ray focus is guided on a segment of a circular path of at least 180° around the examination object;
reconstructing a three-dimensional image of the area of interest from the plurality of X-ray images; and
rotating the support prior to recording each of the plurality of X-ray images around an axis of rotation passing through the X-ray focus, if the area of interest is in a non-centric position, wherein the central point of the circular path is situated non-centrically in the area of interest, and wherein the support is rotated so that a central ray of the X-ray beam for recording the X-ray images passes through the center of the area of interest.

2. The method as claimed in claim 1, wherein the support is guided around the examination object by a robot arm and is rotated around the axis of rotation passing through the X-ray focus.

3. The method as claimed in claim 1, wherein the rotation of the support around the axis of rotation passing through the X-ray focus is synchronized with the guidance of the X-ray focus on the circular path.

4. The method as claimed in claim 2, wherein the rotation of the support around the axis of rotation passing through the X-ray focus is synchronized with the guidance of the X-ray focus on the circular path.

5. The method as claimed in claim 1, wherein the X-ray beam is adjusted based on collimation to a size of the area of interest.

6. The method as claimed in claim 1, wherein a plurality of scans are taken with the area of interest in different positions and with identical positions of the X-ray focus during recording of the X-ray images.

7. The method as claimed in claim 6, wherein the image data for the X-ray images recorded at the same position of the X-ray focus are merged in such a way as if they originated from a single image taken with a sufficiently large detector, whereby a subsequent image reconstruction of a three-dimensional image takes place based upon the merged image data.

8. The method as claimed in claim 7, wherein the different positions of the area of interest are chosen such that the areas of interest from the individual scans overlap.

9. The method as claimed in 1, wherein a scan without collimation or with slight collimation of the X-ray beam and one or more further scans with greater collimation of the X-ray beam are carried out at identical positions of the X-ray focus during recording of the X-ray images.

10. The method as claimed in 9, wherein the scan without collimation or with slight collimation is carried out at a lower X-ray dose than the one or more further scans.

11. The method as claimed in 10, wherein the image data for the X-ray images recorded at the same position of the X-ray focus are merged, wherein the merging takes place for matching image areas by means of weighted averaging, during which the image data from the scan or the further scans receives a higher weighting than the image data from the scan without collimation or with slight collimation, and wherein a subsequent image reconstruction of a three-dimensional image takes place based on the merged image data.

12. An X-ray imaging system, comprising:
an arched support;
an X-ray source mounted to the support;
an X-ray detector mounted to the support, wherein the X-ray source is opposite to the X-ray detector, wherein the X-ray source and the X-ray detector are mounted to the support so that an X-ray beam emitted from an X-ray focus of the X-ray source strikes the X-ray detector, wherein the support is secured to a manipulator arm, wherein the support is moveable around an examination object positioned between the X-ray source and the X-ray detector; and a control unit to control the manipulator arm during X-ray image recording so that the X-ray focus is guided on a segment of a circular path of at least 180° around the examination object during a scan to record a plurality of X-ray images of an area of interest of the examination object from different projection angles, wherein a three-dimensional image of the area of interest is reconstructable based on the plurality of images, wherein in the case of a non-centric location of the area of interest, wherein the central point of the circular path is situated non-centrically in the area of interest, the support is rotated prior to recording each of the plurality of X-ray images around an axis of rotation passing through the X-ray focus such that a central ray of the X-ray beam passes through the center of the area of interest during the recording.

13. The X-ray imaging system as claimed in claim 12, wherein the manipulator arm is the arm of a robot.

14. The X-ray imaging system as claimed in claim 12, wherein the control unit controls the manipulator arm during the X-ray image recording such that the rotation of the support around the axis of rotation passing through the X-ray focus occurs in synchronism with the guidance of the X-ray focus on the circular path.

15. The X-ray imaging system as claimed in claim 12, wherein an image processing device merges the image data for the X-ray images which have been recorded at the same position of the X-ray focus in such a way as if they originated from a single image taken with a sufficiently large detector, and carries out a subsequent image reconstruction of a three-dimensional image on the basis of the merged image data, wherein a plurality of scans are taken with the area of interest in different positions and with identical positions of the X-ray focus during recording of the X-ray images.

16. The X-ray imaging system as claimed in claim 12, further comprising an image processing device, wherein within a scan without collimation or with slight collimation of the X-ray beam and one or more further scans with greater collimation of the X-ray beam at identical positions of the X-ray focus during recording of the X-ray images, wherein the scan without collimation or with slight collimation is carried out at a lower X-ray dose than the one or more further scans, the image processing device merges the image data for the X-ray images, which are recorded at the same position of the X-ray focus, wherein the merging takes place for matching image areas by means of weighted averaging, during which the image data from the scan or the further scans receive a higher weighting than the image data from the scan without collimation or with slight collimation, and carries out a subsequent image reconstruction of a three-dimensional image on the basis of the merged image data.

* * * * *